United States Patent
Meinel

[11] 3,947,685
[45] Mar. 30, 1976

[54] METHOD AND ARRANGEMENT FOR DETERMINING NITRIC OXIDE CONCENTRATION

[75] Inventor: Helmut Meinel, Stuttgart, Germany

[73] Assignee: Deutsche Forschungs- und Versuchsanstalt fur Luft- und Raumfahrt e.v., Bonn, Germany

[22] Filed: Apr. 3, 1974

[21] Appl. No.: 457,643

[30] Foreign Application Priority Data
Feb. 15, 1974 Germany............................ 2407133

[52] U.S. Cl. ............... 250/373; 250/372; 250/343; 250/345; 356/246
[51] Int. Cl.² ........................................ G01J 1/42
[58] Field of Search .......... 250/343, 344, 345, 372, 250/373; 356/246

[56] References Cited
UNITED STATES PATENTS

| | | | |
|---|---|---|---|
| 2,764,692 | 9/1956 | Miller | 250/373 |
| 2,984,988 | 5/1961 | Berger et al. | 250/373 |
| 3,488,491 | 6/1970 | Schuman | 250/345 |
| 3,588,496 | 6/1971 | Snowman | 250/343 |
| 3,593,023 | 7/1971 | Dodson | 250/343 |
| 3,793,525 | 2/1974 | Burch et al. | 250/343 |
| 3,835,322 | 9/1974 | Komatsu | 250/373 |

Primary Examiner—James W. Lawrence
Assistant Examiner—B. C. Anderson
Attorney, Agent, or Firm—Michael J. Striker

[57] ABSTRACT

A method and arrangement for determining the concentration of nitric oxide in a gas mixture, particularly exhaust gases, wherein a beam from a hollow-cathode tube is directed through a modulator, an absorption cell containing a gas mixture with an unknown concentration of nitric oxide, and a monochromator, to a beam detector. A readout arrangement displaying the concentration of nitric oxide gas is operatively connected to the beam detector.

42 Claims, 6 Drawing Figures

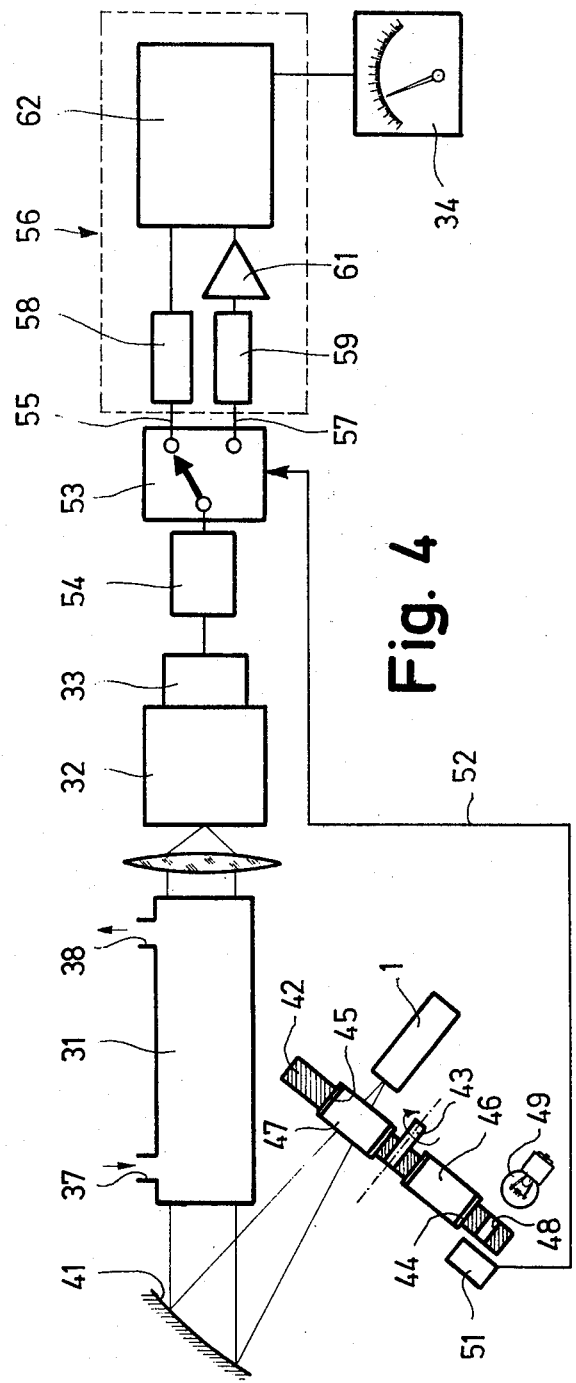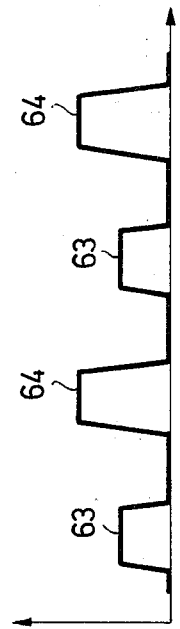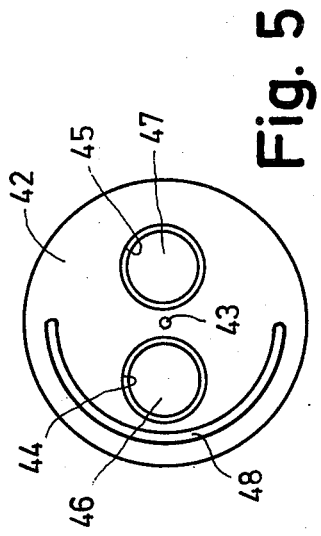

METHOD AND ARRANGEMENT FOR DETERMINING NITRIC OXIDE CONCENTRATION

BACKGROUND OF THE INVENTION

The invention relates to a method and arrangement for determining the concentration of nitric oxide gas in an unknown gas mixture. Such methods are important in industry for the testing and assessment of new motors and gas turbines, which produce unknown exhaust gas mixtures. The arrangements are also utilized for determining air pollution levels in cities and other environments which are subject to pollution from exhaust gases, and contain nitric oxide gas concentrations.

Previous known methods of nitric oxide concentration measurement utilize nondispersive infrared spectroscopy (NDIR) or chemiluminescence methods. The nondispersive infrared spectroscopy method is too inaccurate and too insensitive; the chemiluminescence method is not suitable for the measurement of rapid changes in gas concentrations in exhaust gases. The measurement cell must be operated in a partial vacuum (5 to 10 mm Hg) and requires considerable time, and the complete evacuation of gas. This method also requires permanent production of ozone in normal operation; and an automatic operation is not easily practicable or possible. It is also necessary to calibrate the instrument regularly with no gas mixtures of known concentrations and to correct the values for quenching effects.

SUMMARY OF THE INVENTION

It is an object of the invention to provide a method and an arrangement for determining the concentration of nitric oxide in a gas mixture.

It is another object of the invention to provide a hollow-cathode tube having a can-shaped cathode and an anode, connected to a voltage source, which is useful in analyzing gas mixtures in combination with an absorption cell.

It is another object of the invention to provide a modulator capable of modulating the emitted radiation from the hollow-cathode tube, into two distinct beams corresponding to a reference beam and a measuring beam.

It is another object of the invention to provide for a combination of a hollow-cathode tube, a modulator, and absorption cell, a monochromator, and a beam detector, which may be utilized to determine the relative concentration of a particular molecule in a gas mixture.

It is another object of the invention to provide a novel and improved hollow-cathode tube including a dosage valve, connected to an air intake of the tube, and an exit or air outlet connected with a vacuum pump.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 4 is a schematic diagram of an apparatus according to the teachings of the present invention, in which a hollow-cathode tube is utilized with a measuring and a reference light beam;

FIG. 5 is a top view of a modulator for the device seen in FIG. 4, according to the principles of the present invention; and FIG. 6 is an intensity vs. time diagram of the input to the decoder representing an electrical signal as found in the present invention.

DESCRIPTION OF THE PREFERRED EMBODIMENTS

Figure 1:
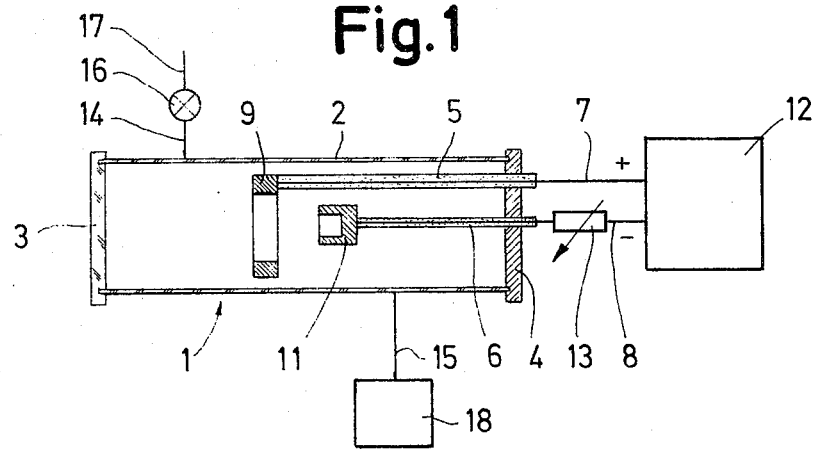
FIG. 1 illustrates a hollow-cathode tube constructed to the teachings of the present invention.

FIG. 1 shows a hollow-cathode tube 1, which produces radiative emissions from excited nitric oxide molecules according to the principles of the present invention. The tube is constructed from a cylindrical glass body 2 with a quartz window 3 at one end, and closed at the other end by a cover 4. Through the cover 4 are passed two ceramic tubes, 5 and 6, in an air-tight seal, and electrical conductors 7 and 8 are connected to the tubes outside of the glass body 2. In the interior of the glass body 2 is a ring-shaped anode, which is connected with the conductor 7; and a hollow can-shaped cathode 11 connected with the conductor 8. Both electrodes are preferably composed of molybdenum. The anode 9 and the hollow cathode 11 are connected through the conductors 7 and 8 with a voltage source 12, preferably with a stabilized current. Between the hollow cathode 11 and the voltage source 12 is an adjustable resistor 13 connected along the conductor 8. Connected to the air-tight glass body 2 is an intake pipe 14 and an exit or outlet pipe 15 for intake and exit of air. The outer intake pipe 17 of the intake pipe 14 is connected to the outer ambient atmosphere, at normal temperature and pressure; in the pipe 14 is a fine dosage valve including a throttle 16, which adjusts the cross section of the intake pipe 14 in a continuous and variable manner and so regulate the intake of air. The outlet pipe 15 is connected with a vacuum pump 18, through which the glass body 2 can be evacuated of air.

In operation according to the principles of the present invention, the throttling valve 16 is adjusted so that the pressure in the interior of the hollow-cathode tube would be equal to about 0.5 mm Hg. This pressure may be achieved by carefully adjusting the throttling valve 16 until the desired pressure is attained.

Figure 3:
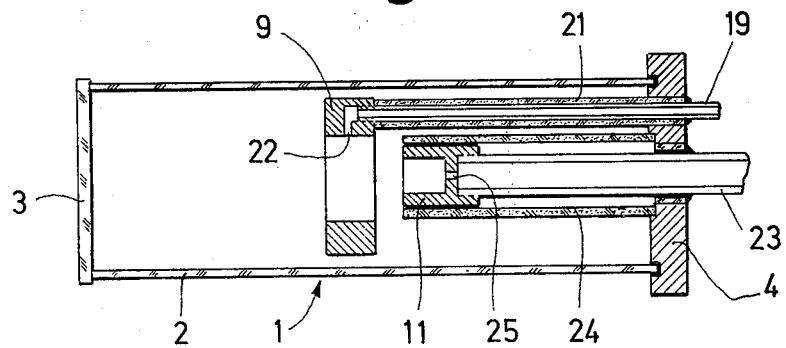
FIG. 3 illustrates a cross section of another embodiment of the hollow-cathode tube according to the present invention.

FIG. 3 is another embodiment of the hollow-cathode tube according to the principles of the present invention. It is constructed in the same manner as the hollow-cathode tube in FIG. 1, and the same numerals refer to like parts. The electrical conductors and the electrodes are, however, somewhat different than the corresponding parts of the hollow-cathode tube of FIG. 1. Connected with the anode 9 is an electrical conductor 19 comprising a thin tube, preferably made of high quality steel. The steel tube 19 is surrounded by an insulating ceramic cover 21, and passes through the cover 4 via an air-tight seal. The inner cavity of the tube-shaped conductor 19 is connected with a bore hole 22 in the anode 9, and thereby into the inner part of the hollow-cathode tube.

The conductor of the hollow-cathode 11 is also constructed of a tube 23, also composed preferably of fine steel. The conductor is also surrounded by a ceramic cover 24, having a relatively large inner diameter, such that it surrounds the side faces of the hollow cathode 11 itself. The conductor 23 passes through the cover 4 through an air-tight seal. On the base plate of the can-shaped hollow cathode 11 is a bore 25 having a diameter of preferably less than 1 mm.

The electrically conducting tubes 19 and 23 are in this embodiment not only the electrical conductors for the anode 9 and the hollow cathode 11, but also at the same time the air intake and outlet passageways. The tube 19 forms the air intake pipe through which air from the outer atmosphere can be directed through the bore 22 into the interior of the hollow cathode lamp 1. Similarly, the tube-like conductor 19 serves the same purpose as the tube 14 in FIG. 1 with a closable dosage valve, which, however, is not explicitly shown in FIG. 3. The tube-like conductor 23 serves as the exit or outlet tube for the air in the interior of the hollow-cathode tube. It is, therefore, similar to the exit tube 15 in FIG. 1, with which a vacuum pump is connected, which, however, is not shown in FIG. 3.

The conductors 19 and 23 operate in the same manner as the conductors 7 and 8 in the hollow-cathode tube of FIG. 1, in which there is shown a source of voltage, and a variable resistor connected between the negative lead of the voltage source and the conductor to the cathode, corresponding to conductor 23. These elements are not explicitly shown in FIG. 3.

The operation of the hollow-cathode tube is as follows. Air is admitted into the interior of the hollow-cathode tube 1 by means of the dosage valve 16, which together with the operation of the vacuum pump, permits an operating pressure of about 0.5 mm Hg. At the same time the voltage source will produce in the interior of the hollow-cathode tube a cathode current, which according to the invention is relatively small. The value of this current lies in the range of a milliampere. Through the apparatus as taught by the present invention, and through a series of intermediate steps, nitric oxide molecules will form from the nitrogen and oxygen in the air. In doing so, an excited state of the molecules will be attained. In the passage from these excited states to the ground state of the nitric oxide molecule, radiation will be emitted, which will be utilized in determining and analyzing the proportion of nitric oxide in a gas mixture.

It is essential that due to the small cathode current and low power dissipation an excessive rise in temperature of the gases within the hollow-cathode tube is avoided. The power of the tube lies in the range of about 0.3 watts. The temperature of the radiating gases is substantially at room temperature, as can be ascertained from an examination of the "rotational temperature" determined by the nitric oxide radiation. The hollow-cathode tube produces a measuring and a reference beam which will be described in detail below. The present invention also provides a practically unlimited lifetime for the hollow-cathode tube, which is significantly important for a nitric oxide measuring device.

Another advantage of the hollow-cathode tube is that the emission of the nitric oxide molecules is free of any background radiation, which may be due to other substances in the tube, such as other gases, or atoms released from the electrode material. The desired intensity of the emitted nitric oxide molecular radiation is optimally achieved through a continual passage of fresh air through the tube. In such a case, the following values are attained:

Noise level less than 0.2%
Long term drift per day less than 1%.

Figure 2:
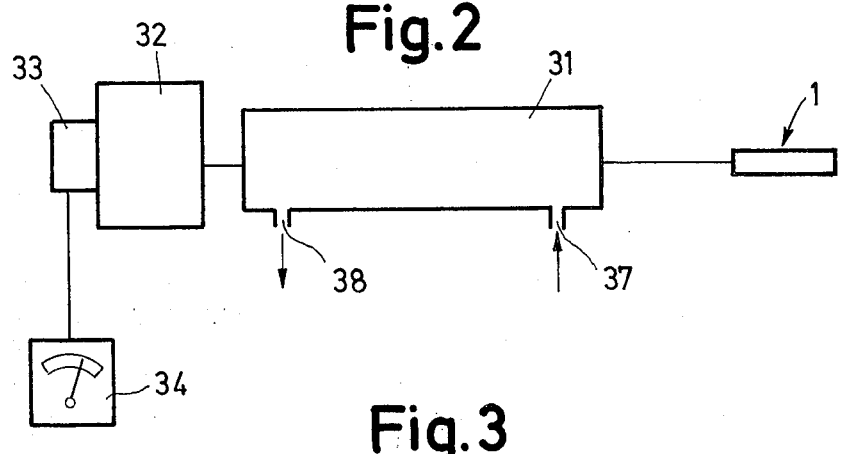
FIG. 2 is a schematic diagram of an arrangement for measuring the nitric oxide level in a test chamber or absorption cell.

FIG. 2 is a simplified block diagram of the arrangement for analyzing a gas mixture as taught by the present invention. There is illustrated the hollow-cathode tube 1, as described above, an absorption cell 31, a monochromator 32, a beam detector 33, and a readout indicator 34.

The absorption cell 31 comprises a container made of special quartz glass, through which the beams emanating from the hollow-cathode tube 1 are passed. The absorption cell 31 includes an inlet 37 and an outlet 38 through which the gas mixtures to be analyzed are passed. The monochromator 32 is transparent to radiation of a particular wavelength, particularly the wavelength of a resonance band of the nitric oxide molecular radiation. The resonance band wavelength is preferably at 2269 Angstroms. The monochromator has a band width of about 20 Angstroms. An interference filter may be also utilized at this point of the apparatus. The beam detector 33 is, for example, a commercially available photomultiplier, which translates the intensity of the incoming radiation into proportional electrical signals.

In operation, the hollow-cathode tube will emit radiation corresponding to transitions between rotational energy levels in the electronically excited and ground state nitric oxide molecules. This radiation will be directed onto the absorption cell 31, and then through the monochromator 32, and finally into the beam detector 33, wherein the resulting intensity will be reflected by proportional indications on a readout device. A focussing lens may be placed before the monochromator 32. In this manner, it is possible to analyze the gas mixtures present in the absorption cell 31, in that the presence of nitric oxide molecules in the absorption cell will respond by resonance absorption to the radiation emitted from the hollow-cathode tube. The nitric oxide molecules in the absorption cell will thereby become excited, absorbing a portion of the radiation emitted by the hollow-cathode tube, and preventing that portion from reaching the monochromator 32 and detector 33. Thus, a smaller amount of radiation will pass through the monochromator 32 and the detector 33 than in the case in which there were no nitric oxide present in the absorption cell 31. This decreased intensity of radiation as reflected by lower intensity values indicated on the readout device 34, is a direct measure of the concentration of nitric oxide in the analyzed gas mixture.

Accordingly, the determination of the nitric oxide molecule concentration in the analyzed gas mixtures is achieved by means of resonance absorption of radiation, a technique which is very specific and accurate for the molecules in question. Furthermore, it is possible by means of a monochromator with a relatively large band width of 20 Angstroms, or a corresponding narrow band width interference filter, to construct an analyzing arrangement which is essentially very simple.

Possible interference absorption, such as through continuous molecular spectra, is compensated for by means of an arrangement according to the teachings of the present invention. The arrangement is illustrated in FIGS. 4 and 5. The interfering absorptions can be due to other molecules or particles located on the surfaces or in the interior of the absorption cell 31. The arrangement consists of placing a modulating unit 42 and a deflecting concave mirror 41 in the path of the radiation emitting from the hollow-cathode tube 1. The axis of rotation of the modulator 42 is essentially parallel to the axis of the emitted radiation from the hollow-cathode tube 1. The axis of the modulator is indicated by the numeral 43. The modulator comprises two recesses 44, 45 along the diameter of the modulator 42, in which are placed cuvettes 46 and 47, respectively. Both cuvettes 46 and 47 are constructed similarly of a cylindrical container in which the end faces are made of ultraviolet-transparent windows of special quartz glass. One of the cuvettes, for example cuvette 46, is filled and closed with nitric oxide gas, preferably at atmospheric pressure. The other cuvette 47 is open and contains air. The thickness of the gas layer in the cuvettes is betweeen 2 and 3 mm.

The modulator 42 is driven around its axis 43 by means of a synchronous motor (not shown) at a rate of from 10 to 50 rps. The modulator is so arranged so that the gas cuvettes 46 and 47 periodically appear in front of the hollow-cathode tube 1, so that the emitted radiation from the hollow-cathode tube is transmitted through one or the other of the gas cuvettes. The result is that two beams then impinge on the absorption chamber 31, one which has passed through a nitric oxide gas in the cuvette 46, and thereby represents a "filtered" beam, and another beam which has not passed through any nitric oxide gas. These two beams will be referred to as the "reference beam" and the "measuring beam", respectively.

Both cuvettes 46 and 47 are constructed in the same manner. Thereby the effects of absorption, reflection and scattering of the quartz glass windows of the cuvettes will be taken into account. It is also within the conception of the invention to provide other gases within the cuvette 47, or to utilize an evacuated cuvette 47. The essential point of the invention is to permit a hollow-cathode tube 1 to generate a sequence of signals, corresponding to sequential measuring and reference beams of light. The spectral difference between the beams reflects the fact that the reference beam has passed through a volume of nitric oxide gas whereas the measuring beam has not done so.

The modulator 42 also comprises a slit 48 extending circumferentially over half of the circular face 42. On one side of the modulator 42 is a lamp 49, located behind the region of the slit 48 and on the other side of the modulator 42 is a light sensitive detector, such as a photocell 51. When the modulator 42 is rotated, the slit transmits light through the modulator from the lamp 49 to the photocell 51, during which time the radiation from the hollow-cathode tube 1 is passing through the cuvette 47 the light striking the photocell 51 generates an electrical pulse signal. When the radiation is passing through the other cuvette 46, the light from the bulb 49 is shielded since the slit does not continue on the opposite side of the modulator 42, and therefore no electrical signal is generated from photocell 51. A pulse is emitted when cuvette 47 lies in the path of the radiation from the hollow-cathode tube.

The slit 48 is so arranged to produce a series of pulses corresponding to the rotation of the modulator, and thereby corresponding to the nature of the emitted light coming from the modulator.

The photocell 51 is connected to a conducting wire 52 and thereupon into a decoder 53. The elements of the arrangement 31, 32 and 33 have been previously described in FIG. 2. The output from the photomultiplier 33 is connected to an amplifier 54 and thereby to the decoder 53. The decoder 53 has two possible outputs 55 and 57, both outputs 55 and 57 are connected to a control and storage unit 56. The decoder acts in a well known manner to apply the measured signal (corresponding to the measuring beam) to the output line 55, and the reference signal (corresponding to the reference beam) to the output line 57. The measuring signal is applied to a storage element 58, the reference signal applied to a storage element 59 and thereby to an amplifier 61, and both signals, connected with an electrical divider 62, the output of which is connected to the readout device 34.

The operation of the arrangement is as follows.

The absorption cell 31 is filled and continuously supplied with the nitric oxide containing gas to be analyzed. The essentially unfiltered measuring beam will be directed into the absorption cell 31 and react with the nitric oxide molecules therein. The rotation of the modulator disc 42 results in directing either the measuring beam or the reference beam onto the absorption cell. The beam coming from the cuvette 46 filled with NO gas results in the reference beam; the beam coming from the cuvette 47 which is filled with air results in the measuring beam. The reference signal is so-called because its intensity should not be effected by the presence of nitric oxide gas in the absorption cell. Therefore any diminution of the reference signal as it passes through the absorption cell is due to additional interference or absorption with other molecules, such as from particles in the gas mixture, an additional molecular absorption of the analyzed gases, or contamination of the windows of the absorption cell itself. The decoder 53 then serves to distinguish the reference signal and the measuring signal by means of the opening or closing of the photocell 51, so that the two distinct signals, arising from the two distinct beams, are applied to different and distinct storage cells 58 and 59.

FIG. 6 is a time and intensity graph of the reference signal 63 and the measuring signal 64. It is clear that since the reference signal has been obtained from the reference beam, which has passed through the nitric oxide containing cuvette, that this signal is smaller in intensity than the measuring signal 64. Reference signal 63 therefore represents the "background" whereas the measuring signal 64 represents the nitric oxide levels in the absorption cell. These two signals are then separated by the decoder 53 and each applied to a storage cell 58, 59. The reference signal is also applied to another amplifier 61. The divider 62 then forms the quotient of the signals 64 and 63, which is then displayed on the readout device 34. The display on the readout device 34 of this so determined quotient is a measure of the nitric oxide concentration in the analyzed gas mixture.

The method of the invention depends on the measuring and the reference beams coming from the hollow-cathode tube 1. The measuring beam entering the absorption cell is essentially unfiltered, whereas the reference beam has passed through a cuvette of nitric oxide gas and the beam has been subject to considerable absorption. It is utterly essential for the invention that the beams passing through the nitric oxide cuvette and through the air cuvette have essentially the same spectral characteristics. This is made possible by the specific excitation mechanism of the hollow-cathode discharge as taught by the present invention. The rotational energy distribution within the electronically excited state of NO is identical with a distribution which would be obtained by heating up NO gas to 1500° Kelvin. It is therefore said that the emitting nitric oxide molecules have a "population temperature" of rotational energy levels of 1500° Kelvin. On the other hand, the gas temperature of the emitting nitric oxide molecules lies at about room temperature (300° Kelvin) since the hollow-cathode tube ist operated at very low power input, such as 0.3 watts. Therefore, the emitted beams consist of a number of rotational spectral lines whose rotational distribution corresponds to a temperature of 1500° Kelvin while the Doppler-profile of each individual rotational line corresponds to a temperature of 300° Kelvin.

However, rotational lines emitted from highly excited rotational states corresponding to the population temperature of 1500° Kelvin cannot be absorbed by "cold" NO molecules characterized by a rotational population temperature of 300° Kelvin. It is on this physical principle that the working of the invention is possible.

The reference beam will pass through the nitric oxide gas volume of the modulator disk and thereby be filtered. As a result a large part of the radiation from the hollow-cathode tube is absorbed. Since the nitric oxide volume in the modulator disk is, at room temperature, which is considerably below the population temperature of the excited molecules, a small part of the radiation, namely emissions from rotational levels with high quantum numbers, will pass through this nitric oxide gas filter without being absorbed. Therefore, the reference beam has an intensity of only about 10% of the intensity of the measuring beam after this absorption process takes place.

The measuring beam is subject to absorption in the absorption cell from the presence of nitric oxide gas. The reference beam does not react to the presence of nitric oxide gas in the absorption cell, and is not absorbed or affected since the temperature of this gas is nearly the same as the temperature of the gas in the cuvette. The gas mixture being analyzed is in general below the population temperature of the excited NO-molecules from the hollow-cathode tube. Due to the complicated spectral structure of NO-molecular transitions, the rotational spectral lines of the reference beam are distributed among the nitric oxide resonance band. The intensity distribution of the reference beam has therefore the same spectral band width as the intensity distribution of measuring beam, and at every point in time is proportional to the intensity of the measuring beam.

If there is additional absorption interference in the absorption cell, such as due to a dirty window plate, or fine particles in the gas mixture, both the measuring beam and the reference beam will be affected in the same proportions. A quotient of the two beams would therefore represent the affect of nitric oxide in the gas mixture, and the interference effects would be cancelled out in the quotient. The effects of absorption from particulate matter, as well as from statistical fluctuations in intensity from the hollow-cathode tube, or other fluctuations arising along the beam path, would be successfully eliminated in the quotient-taking operation.

Although the present invention is described utilizing a resonance band of 2269A in which to take the quotient of the two beams, other resonance bands, such as 2156A, may be used equally as well.

While the invention has been illustrated and described as embodied in a method and arrangement for determining nitric oxide concentration, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

1. A method of determining the concentration of nitric oxide (NO) in a gas mixture of unknown composition, particularly exhaust gas, comprising the steps of pumping air through a hollow-cathode tube and keeping the air pressure therein subatmospheric; continuously producing in the tube, from the nitrogen and oxegen in the air passing therethrough, excited nitric oxide molecules which emit radiation consisting of a plurality of discrete rotational spectral lines, by applying a potential difference across the anode and cathode of the tube and operating the tube at a current having an order of magnitude of about 1 milliampere; directing a beam of such radiation through said gas mixture so that such radiation becomes attentuated due to resonance absorption by nitric oxide molecules in said gas mixture; and measuring said attenuation.

2. A method as defined in claim 1, wherein said step of pumping air comprises keeping the air pressure in the tube at about 1 mm Hg.

3. A method as defined in claim 1, wherein said step of measuring said attenuation comprises filtering the attenuated radiation using a filter which passes radiation in the frequency range of a resonance band of the radiation produced by said excited nitric oxide molecules.

4. A method as defined in claim 3, wherein said resonance band has a bandwidth of 20 Angstroms and is located at a wavelength of 2269 Angstroms.

5. A method as defined in claim 1, wherein said step of directing such radiation through said gas mixture comprises confining said gas mixture in an absorption cell.

6. A method as defined in claim 1, wherein said step of directing comprises directing through said gas mixture a reference beam formed by directing radiation emitted from the hollow-cathode tube through a filter before passage through said gas mixture, using for the filter a chamber filled with nitric oxide having a temperature lower than the population temperature of the excited nitric oxide molecules in the hollow-cathode tube, and at a different time directing through said gas mixture a measuring beam obtained by directing through the gas mixture radiation emitted from the hollow-cathode tube but without prior passage through said filter, wherein said step of measuring comprises measuring the respective intensities of the reference beam and of the measuring beam, and forming the ratio of the two intensities, said ratio representing the concentration of nitric oxide in said gas mixture.

7. A method as defined in claim 6, wherein said step of directing further comprises passing said reference beam and said measuring beam through said gas mixture alternately and periodically.

8. A method as defined in claim 6, wherein the forming of said reference beam and of said measuring beam is accomplished using a modulator disk located in the path of radiation emitted from the hollow-cathode tube and travelling towards said gas mixture.

9. A method as defined in claim 7, wherein the passing of said reference beam and of said measuring beam through said gas mixture alternately and periodically is accomplished by passing the radiation emitted from the hollow-cathode tube and travelling towards said gas mixture alternately and periodically through a filter comprised of a cuvette filled with air and through a cuvette filled with nitric oxide.

10. A method as defined in claim 6, wherein said step of measuring further comprises sensing said intensities and generating corresponding electrical signals, and processing said signals to generate a resultant signal corresponding to the ratio of said intensities, said ratio representing the concentration of nitric oxide in said gas mixture.

11. A method as defined in claim 10, wherein said step of measuring further comprises storing at least some of said electrical signals in a signal storage element.

12. An arrangement for measuring the concentration of nitric oxide (NO) in a gas mixture of unknown composition, comprising, in combination, a hollow-cathode tube comprised of a container having an inlet and an outlet and an anode and a can-like cathode in the container; pump means for pumping air through said tube; valve means connected to said inlet operative for keeping the air pressure in said tube subatmospheric; means for effecting continuous conversion of nitrogen and oxygen in the air passing through said tube into excited nitric oxide molecules which emit to outside said tube radiation consisting of a plurality of discrete rotational spectral lines; a radiation detector located in the path of the radiation emitted from said tube by said excited nitric oxide molecules; and in the path of said radiation intermediate said tube and said detector an absorption cell for holding said gas mixture.

13. An arrangement as defined in claim 12, wherein said means for effecting the conversion of nitrogen and oxygen in the air in said tube into excited nitric oxide comprises means for establishing a potential difference across said anode and cathode and for establishing therebetween a current on the order of magnitude of one milliampere.

14. An arrangement as defined in claim 12, wherein said radiation detector is a photomultiplier.

15. An arrangement as defined in claim 12, further including a monochromator positioned in the path of said radiation intermediate said absorption cell and said detector.

16. An arrangement as defined in claim 12, wherein said can-like cathode has a bore, said outlet being constructed of metal and connected to said bore.

17. An arrangement as defined in claim 16, wherein said metal outlet and said can-like cathode are electrically conductively connected to each other, and wherein said means for effecting conversion includes a voltage source electrically connected to said anode and to said metal outlet for establishing a potential difference between said anode and cathode with the cathode current flowing through said metal outlet.

18. An arrangement as defined in claim 12, whrein said inlet is made of metal and connected to said anode.

19. An arrangement as defined in claim 18, wherein said metal inlet and said anode are electrically conductively connected to each other, and wherein said means for effecting conversion includes a voltage source electrically connected to said cathode and to said metal inlet for establishing a potential difference between said anode and cathode with the anode current flowing through said metal inlet.

20. An arrangement as defined in claim 12, further comprising modulator means interposed between said hollow-cathode tube and said absorption cell, for producing a measuring beam and a reference beam.

21. An arrangement as defined in claim 20, wherein said modulator means comprises two filters, the first filter being a cuvette filled with air, the second filter being a cuvette filled with nitric oxide, said filters being at least part of the time in the path of said radiation.

22. An arrangement as defined in claim 21, wherein said filters are sequentially and periodically interposed in the path of said radiation, said radiation passing through said first filter producing said measuring beam, said radiation passing through said second filter producing said reference beam.

23. An arrangement as defined in claim 21, wherein said modulator means further comprises signal means for producing electrical pulse signals indicating which of said two filters are in the path of said radiation.

24. An arrangement as defined in claim 23, wherein said beam detector produces electrical output signals in response to the intensity of said radiation directed at said detector; and further comprises decoding means, having an input and two outputs, said input being connected with said electrical output signals, said two outputs being connected to a divider, either of said two outputs being selected by said decoding means on the basis of said electrical pulse signals from said signal means.

25. An arrangement as defined in claim 15, wherein said monochromator operates in the range of the resonance band at 2269 Angstroms.

26. An arrangement as defined in claim 23, wherein said modulator means is a rotatable disk, whose axis of rotation is parallel to the direction of said emitted radiation.

27. An arrangement as defined in claim 21, wherein said cuvette filled with nitric oxide is at atmospheric pressure.

28. An arrangement as defined in claim 21, wherein said cuvettes are cylindrically shaped, having two end faces, said faces comprising windows capable of transmitting ultraviolet radiation.

29. An arrangement as defined in claim 21, wherein the gas layer in said cuvettes is between 2 and 3 mm thick.

30. An arrangement as defined in claim 21, wherein said disk comprises a slit extending circumferentially over half of the face of the disk; and wherein said signal means comprise a light source located on one side of said disk in the region of said slit and photocell means on the other side of said disk in the region of said slit, responsive to said light source to produce said pulse signals.

31. An arrangement as defined in claim 30, wherein said photocell means are responsive to said light source when said cuvette filled with air is disposed in the path of said radiation.

32. A method of determining the concentration of nitric oxide (NO) in a gas mixture of unknown composition, particularly exhaust gas, comprising the steps of generating radiation consisting of a plurality of discrete rotational spectral lines emitted from excited nitric oxide molecules; directing a beam of such radiation through said gas mixture so that such radiation becomes attenuated due to absorption by nitric oxide molecules in said gas mixture; and measuring the attenuation.

33. A method as defined in claim 32, wherein said step of directing comprises directing through said gas mixture a reference beam formed by directing radiation emitted by said excited nitric oxide molecules through a filter prior to passage through said gas mixture, using for the filter a chamber filled with nitric oxide having a temperature lower than the population temperature of the radiation-emitting excited nitric oxide molecules, and directing through said gas mixture a measuring beam composed of radiation emitted by said excited nitric oxide molecules but without prior passage through said filter, wherein said step of measuring comprises measuring the respective intensities of the reference beam and of the measuring beam, and forming the ratio of the two intensities, said ratio representing the concentration of nitric oxide in said gas mixture.

34. A method as defined in claim 32, wherein said step of generating radiation comprises generating said excited nitric oxide molecules from nitrogen and oxygen in air.

35. A method as defined in claim 32, wherein said step of generating radiation comprises establishing a stream of air and at a predetermined location in said stream continuously generating said excited nitric oxide molecules from nitrogen and oxygen in the streaming air.

36. A method as defined in claim 32, wherein said step of generating radiation comprises establishing a stream of air through a container, and continuously converting nitrogen and oxygen in the air in said container into said excited nitric oxide molecules while removing the formed nitric oxide molecules from the container at the same rate as they are produced.

37. A method as defined in claim 34, wherein said generating of excited nitric oxide molecules from nitrogen and oxygen in air comprises establishing in said air a discharge having a discharge current on the order of magnitude of about one milliampere.

38. An arrangement for measuring the concentration of nitric oxide (NO) in a gas mixture of unknown composition, comprising, in combination, means for generating radiation consisting of a plurality of discrete rotational spectral lines emitted from excited nitric oxide molecules; means for directing a beam of such radiation through said gas mixture so that such radiation becomes attenuated due to absorption by nitric oxide molecules in said gas mixture; and means for measuring said attenuation.

39. An arrangement as defined in claim 38, wherein said means for generating radiation comprises means operative for generating said excited nitric oxide molecules from nitrogen and oxygen in air.

40. An arrangement as defined in claim 38, wherein said means for generating radiation comprises means for establishing a stream of air and means operative for continuously generating at a predetermined location in said stream said excited nitric oxide molecules from nitrogen and oxygen in the streaming air.

41. An arrangement as defined in claim 38, wherein said means for generating radiation comprises a container, means for continuously converting nitrogen and oxygen in any air in said container into excited nitric oxide molecules, and air-flow-establishing means for continuously supplying fresh air into said container while removing previously supplied air and the generated nitric oxide molecules therein at a rate corresponding to the rate at which the excited nitric oxide molecules are produced.

42. An arrangement as defined in claim 39, wherein said means for generating excited nitric oxide molecules from nitrogen and oxygen in air comprises means for establishing in said air a discharge having a discharge current on the order of magnitude of about one milliampere.

* * * * *